US009725521B2

United States Patent
Liu et al.

(10) Patent No.: US 9,725,521 B2
(45) Date of Patent: Aug. 8, 2017

(54) HUMAN-DERIVED INSECTICIDAL GENE AND INSECTICIDAL PEPTIDE ENCODED THEREBY AND APPLICATION THEREOF

(71) Applicant: JIANGSU ACADEMY OF AGRICULTURAL SCIENCES, Xuanwu Nanjing (CN)

(72) Inventors: Xianjin Liu, Xuanwu Nanjing (CN); Yuan Liu, Xuanwu Nanjing (CN); Yajing Xie, Xuanwu Nanjing (CN); Aihua Wu, Xuanwu Nanjing (CN); Xiao Zhang, Xuanwu Nanjing (CN); Chongxin Xu, Xuanwu Nanjing (CN); Yanyan Zhao, Xuanwu Nanjing (CN); Jianfeng Zhong, Xuanwu Nanjing (CN)

(73) Assignee: JIANGSU ACADEMY OF AGRICULTURAL SCIENCES, Xuanwu Nanjing (CN)

( * ) Notice: Subject to any disclaimer, the term of this patent is extended or adjusted under 35 U.S.C. 154(b) by 0 days.

(21) Appl. No.: 15/103,515

(22) PCT Filed: Jan. 9, 2015

(86) PCT No.: PCT/CN2015/070423
§ 371 (c)(1),
(2) Date: Jun. 10, 2016

(87) PCT Pub. No.: WO2016/086513
PCT Pub. Date: Jun. 9, 2016

(65) Prior Publication Data
US 2017/0088633 A1 Mar. 30, 2017

(30) Foreign Application Priority Data

Dec. 5, 2014 (CN) .......................... 2014 1 0735997

(51) Int. Cl.
*C07K 16/42* (2006.01)
*C07K 16/12* (2006.01)
*A01N 63/02* (2006.01)

(52) U.S. Cl.
CPC .......... *C07K 16/4233* (2013.01); *A01N 63/02* (2013.01); *C07K 16/1278* (2013.01); *C07K 2317/21* (2013.01); *C07K 2317/622* (2013.01); *C07K 2317/73* (2013.01)

(58) Field of Classification Search
None
See application file for complete search history.

(56) References Cited

FOREIGN PATENT DOCUMENTS

| CN | 103571853 A | 2/2014 |
|---|---|---|
| CN | 103757049 A | 4/2014 |
| CN | 103773775 A | 5/2014 |
| WO | 2010141953 A2 | 12/2010 |

OTHER PUBLICATIONS

Li Hai-Tao et al., Cloning and Expression of cry2Aa Genes from Isolates of Bacillus thuringienis and Their Bioactivity, Journal of Agricultural Biotechnology, pp. 1-5, Dec. 31, 2012, vol. 28, No. 4.
Xu Chong-Xin et al., Screening and Identification of Single-Chain Antibodies (scFvs) Against Baciullus thuringiensis Cry1B Toxin, Jiangsu Journal of Agricultural Sciences, pp. 886-890, Dec. 31, 2012, vol. 28, No. 4.
Yun Wang et al., Isolation of Single Chain Variable Fragment (scFv) Specific for Cry1C toxin from human single fold scFv libraries, Toxicon, Sep. 5, 2012, vol. 60, No. 7.
International Search Report, PCT/CN2015/070423, Dated Jul. 15, 2015.

*Primary Examiner* — Robert A Zeman
(74) *Attorney, Agent, or Firm* — Heslin Rothenberg Farley & Mesiti P.C.

(57) ABSTRACT

The present invention discloses a human-derived insecticidal gene and insecticidal peptide encoded by the same and application thereof. The nucleotide sequence of the human-derived insecticidal gene is as represented by SEQ ID NO.1. The amino acid sequence of the insecticidal peptide encoded by this gene is as represented by SEQ ID NO.2. The insecticidal peptide may be expressed through prokaryotic system. The primary culture has binding activity to *Cnaphalocrocis medinalis* midgut peritrophic membrane specific receptor BBMV. It is obtained without animal immunization and has a short production cycle and a small amino acid sequence. It is suitable for in vitro mass production and may lower the safety risks resulting from wide use of existing Bt toxins and even might substitute Bt to biologically control agricultural pests in the future. It has important scientific and practical significance to reducing the use of insecticides.

2 Claims, 2 Drawing Sheets

SEQUENCE LISTING

```
<160> NUMBER OF SEQ ID NOS: 2

<210> SEQ ID NO 1
<211> LENGTH: 1000
<212> TYPE: DNA
<213> ORGANISM: Artificial Sequence
<220> FEATURE:
<223> OTHER INFORMATION: Artifically synthesized

<400> SEQUENCE: 1
ccggcccttt ggcatgcaat ttctatttca ggagacagtc ataatgaaat acctattgcc      60
tacggcagcc gctggattgt tattactcgc ggcccagccg gccatggccg aggtgcagct     120
gttggagtct gggggaggct tggtacagcc tgggggggtcc ctgagactct cctgtgcagc     180
ctctggattc acctttagca gctatgccat gagctgggtc cgccaggctc cagggaaggg     240
gctggagtgg gtctcaagta ttgattctta tggtactaat acagattacg cagactccgt     300
gaagggccgg ttcaccatct ccagagacaa ttccaagaac acgctgtatc tgcaaatgaa     360
cagcctgaga gccgaggaca cggccgtata ttactgtgcg aaagctttta attcttttga     420
ctactggggc cagggaaccc tggtcaccgt ctcgagcggt ggaggcggtt caggcggagg     480
```

| | | | | | |
|---|---|---|---|---|---|
| tggcagcggc ggtggcgggt cgacggacat ccagatgacc cagtctccat cctccctgtc | | | | | 540 |
| tgcatctgta ggagacagag tcaccatcac ttgccgggca agtcagagca ttagcagcta | | | | | 600 |
| tttaaattgg tatcagcaga accagggaaa gcccctaag ctcctgatct atgctgcatc | | | | | 660 |
| cgctttgcaa agtggggtcc catcaaggtt cagtggcagt ggatctggga cagatttcac | | | | | 720 |
| tctcaccatc agcagtctgc aacctgaaga ttttgcaact tactactgtc aacagtatag | | | | | 780 |
| ttctagtcct tctacgttcg gccaagggac caaggtggaa atcaaacggg cggccgcaca | | | | | 840 |
| tcatcatcac catcacgggg ccgcagaaca aaaactcatc tcagaagagg atctgaatgg | | | | | 900 |
| ggccgcatag actgttgaaa gttgtttagc aaaacctcat acagaaaatt catttactaa | | | | | 960 |
| cgtctggaaa gacgacaaaa ctttaaatcg ttacgctaac | | | | | 1000 |

<210> SEQ ID NO 2
<211> LENGTH: 288
<212> TYPE: PRT
<213> ORGANISM: Artificial Sequence
<220> FEATURE:
<223> OTHER INFORMATION: Artificially synthesized

<400> SEQUENCE: 2

```
Met Lys Tyr Leu Leu Pro Thr Ala Ala Ala Gly Leu Leu Leu Leu Ala
1               5                  10                  15

Ala Gln Pro Ala Met Ala Glu Val Gln Leu Leu Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Ser Tyr Ala Met Ser Trp Val Arg Gln Ala Pro Gly
    50                  55                  60

Lys Gly Leu Glu Trp Val Ser Ile Asp Ser Tyr Gly Thr Asn Thr
65                  70                  75                  80

Asp Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Lys Ala Phe Asn Ser Phe Asp Tyr Trp
        115                 120                 125

Gly Gln Gly Thr Leu Val Thr Val Ser Ser Gly Gly Gly Gly Ser Gly
    130                 135                 140

Gly Gly Gly Ser Gly Gly Gly Gly Ser Thr Asp Ile Gln Met Thr Gln
145                 150                 155                 160

Ser Pro Ser Ser Leu Ser Ala Ser Val Gly Asp Arg Val Thr Ile Thr
                165                 170                 175

Cys Arg Ala Ser Gln Ser Ile Ser Ser Tyr Leu Asn Trp Tyr Gln Gln
            180                 185                 190

Lys Pro Gly Lys Ala Pro Lys Leu Leu Ile Tyr Ala Ala Ser Ala Leu
        195                 200                 205

Gln Ser Gly Val Pro Ser Arg Phe Ser Gly Ser Gly Ser Gly Thr Asp
    210                 215                 220

Phe Thr Leu Thr Ile Ser Ser Leu Gln Pro Glu Asp Phe Ala Thr Tyr
225                 230                 235                 240
```

-continued

```
Tyr Cys Gln Gln Tyr Ser Ser Ser Pro Ser Thr Phe Gly Gln Gly Thr
                245                 250                 255

Lys Val Glu Ile Lys Arg Ala Ala Ala His His His His His His Gly
            260                 265                 270

Ala Ala Glu Gln Lys Leu Ile Ser Glu Glu Asp Leu Asn Gly Ala Ala
        275                 280                 285
```

HUMAN-DERIVED INSECTICIDAL GENE AND INSECTICIDAL PEPTIDE ENCODED THEREBY AND APPLICATION THEREOF

CROSS REFERENCE TO RELATED APPLICATIONS

This application is a national stage filing under section 371 of International Application No. PCT/CN2015/070423, filed on Jan. 9, 2015, and claims priority of Chinese application no. 201410735997.5, filed on Dec. 5, 2014, the entire disclosure of these applications being hereby incorporated herein by reference.

SEQUENCE LISTING

This application contains a Sequence Listing in Computer Readable Form; the file, in ASCII format, is designated H0713014.txt, which is 4.3 kilobytes in size and was created on Oct. 5, 2015. The sequence listing file is hereby incorporated by reference in its entirety into the application.

FIELD OF THE INVENTION

The present invention relates to genetic engineering and biological control field, particularly to a human-derived insecticidal gene and insecticidal peptide encoded by the same and application thereof.

BACKGROUND OF THE INVENTION

Currently, the insecticidal gene widely used in the world for biological control of pests is Bt toxin gene of *Bacillus thuringiensis* (Bt) (such as: Cry1C, Cry1Ab, Cry1B, Cry1F and Cry2Aa, etc.). *Bacillus thuringiensis* is insect pathogenic bacterium. The Bt toxin generated by *Bacillus thuringiensis* has a specific killing effect to many species of agricultural and forestry pests. Since Belgian Plant Genetic Systems first reported the success of transgenic Bt insecticidal tobacco in 1987 till today, Bt gene has been transferred to main crops in the world, such as: maize, paddy, cotton, tomato, potato and tobacco. According to the statistics of International Service for the Acquisition of Agri-biotech Applications (ISAAA) in 2012, the area of transgenic Bt cotton grown in China has exceeded 3.9 million hectares, accounting for 71.5% of the total area of the cotton grown in China. However, following the application and generalization of transgenic Bt crops, its possible potential hazards in gene escape, change of microbial ecological structure of soil, drug resistance of species and harm to normal immune system have gradually aroused the attention of the society. In the academic sector, "Diversity of Rhizospheric Microorganisms and Bacterial Physiological Groups of Transgenic Bt Maize" (Wang Min et al., Chinese Journal of Ecology, Issue 03 of 2010) and "Influence of Transgenic Bt Maize on Bacterial Quantity and Diversity of Soil" (Liu Ling et al., Journal of Ecology and Rural Environment, Issue 03 of 2011) analyzed the bacterial quantity and diversity of the soil in which transgenic Bt maize is grown indoors and outdoors respectively. The results all show significant difference between the transgenic Bt maize growing group and the blank control group. "Cry1Ac protoxin from *Bacillus thuringiensis* sp. *kurstaki* HD73 binds to surface proteins in the mouse small intestine" (Vázquez-Padrón et al., Biochem Biophys Res Commun, Issue 01, 2000) discovered that when intrinsic toxic protein of Bt and extrinsic toxic protein of Bt taken in by a mouse reached 10 mg/kg and 100 mg/kg during animal experiment, T cell ANAE positive rate, spleen index and macrophage phagocytosis of the mouse all were inhibited obviously. The more the intake is, the more obvious the inhibiting effect will be. This experiment also discovered that when the cumulative coefficient of Bt toxin protein in animal body was greater than 6.24, it might result in injury of liver, kidney and gastrointestinal tract and in liver and kidney, anomalies of cellular swelling and vacuolar degeneration could be observed and glomerular vascular epithelial lesion could be seen. Of course, it can't be excluded that they were caused by immunoreactions. Meanwhile, long-term use of Bt toxin protein at a large dose may also result in significant decrease of total white blood cells (WBC) and hemoglobin (HGB) of animals. This also indicates Bt toxin protein has obvious toxicity of immunosuppression. Therefore, developing substitute biological effectors with Bt toxin bioactivity is a research hotspot in biological pest development field.

Insecticidal peptide is a kind of bioactive polypeptide generated in biological bodies through induction. Some Bt insecticidal crystal proteins may be decomposed into insecticidal peptide in insect bodies to realize an insecticidal effect, so it has become a new development direction for substitute biological effectors with Bt toxin bioactivity at present. Anti-idiotype antibody (hereinafter referred to as "Anti-Id") is such a type of polypeptide with a biological insecticidal effect. Anti-Id refers to the specific antibody generated to address the Idiotype (hereinafter referred to as "Id") in the variable regions of antibody molecules. Bona et al. classified Anti-Id into four types ($\alpha$, $\beta$, $\gamma$ and $\epsilon$) based on serological reaction between Id and Anti-Id as well as the function of AId. $\beta$-type Anti-Id has the effect of "internal image", i.e.: has antigenic determinant same as (haptin) antigen, so it may have the functions and bioactivity of antigen.

Currently, phage display technology is universally adopted. By establishing a phage antibody library and through specific screening, Anti-Id with an effect similar to target antigen may be obtained. The process of screening specific antibody by phage display technology is called "Panning" and mainly includes four steps: binding, washing, eluting and amplification. Raats et al. adopted anti-cortisol monoclonal antibody coating as solid-phase antigen for direct screening. Before screening, a same species of negative monoclonal antibody is negatively screened to avoid screening recombinant antibody fragments bound to the constant region of antibody and Anti-Id against cortisol is successfully screened. Goletz et al. also applied phage antibody display system and researched and compared the influence of different elution methods on Anti-Id fragment screening results. Of the eventually screened 96 clones, 28 were positive clones with Anti-Id characteristics. So far, no materials and products specific to substitutable Bt active effector, particularly Anti-Bt toxin type Anti-Id single-chain antibody (hereinafter referred to as "Anti-Id ScFvs") micromolecule polypeptide, have been reported.

CONTENT OF THE INVENTION

To address the potential safety hazard from the extensive application of transgenic Bt toxin crops and toxin preparations thereof, hypersensitivity and other problems at present, the present invention is realized through the provision of Bt toxin bioactivity as well as insecticidal polypeptide encoded thereby:

A human-derived insecticidal gene, having a nucleotide sequence represented by SEQ ID NO.1;

An insecticidal peptide encoded by the human-derived insecticidal gene as described in the present invention, which has an amino acid sequence represented by SEQ ID NO.2;

A prokaryotic vector containing the human-derived insecticidal gene as described in the present invention;

An application of the insecticidal peptide encoded by the human-derived insecticidal gene as described in the present invention in control of agricultural pests;

An insecticide containing the insecticidal peptide encoded by the human-derived insecticidal gene as described in the present invention;

The present invention screened and obtained from the disclosed human gene banks a "β"-type anti-Cry2Aa toxin idiotype single-chain antibody (insecticidal peptide) with insecticidal activity and determined its amino acid sequence and nucleotide sequence. After being expressed by the prokaryotic expression system, the primary culture of the insecticidal peptide has binding activity to Cnaphalocrocis medinalis midgut peritrophic membrane specific receptor BBMV and is obtained without animal immunization. The preparation cycle is short. The amino acid sequence is small. It is suitable for in vitro mass production. Meanwhile, the present invention as a new insecticidal gene resource has important scientific and practical significance to exploring and developing new-type insecticidal gene resources simulating Bt toxin bioactivity to lower the safety risks from the wide use of existing Bt toxins and even substitute Bt in the future in biological control of agricultural pests and reduce the use of insecticides.

DETAILED DESCRIPTION OF THE EMBODIMENTS

Figure 1:
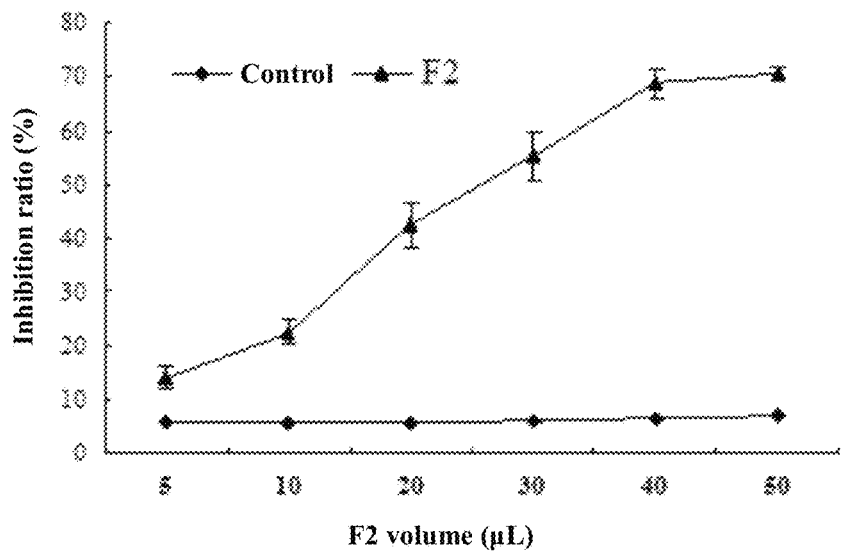
FIG. 1 is a schematic of F2 ELISA detection result.

Reagents and medium formulae involved in the embodiment:

(1) 2×TY fluid medium:
Add 16 g of tryptone, 10 g of yeast extract and 5 g of NaCl in 900 mL of double distilled water, mix them well, set the volume to 1 L by double distilled water, put the liquid in an autoclave, sterilize it at 121° C. for 20 minutes, cool it and store it at 4° C. for future use.

(2) 2×TY-AG fluid medium:
Add ampicillin with final concentration of 100 μg/ml and glucose with a mass ratio of 1% to 2×TY culture medium.

(3) 2×TY-AK fluid medium:
Add ampicillin with final concentration of 100 μg/ml and kanamycin with final concentration of 50 μg/ml to 2×TY culture medium.

(4) 2×TY-AKG fluid medium:
Add ampicillin with final concentration of 100 μg/ml, kanamycin with final concentration of 50 μg/ml and glucose with a mass ratio of 1% to 2×TY culture medium.

(5) TYE solid medium:
Add 15.0 g of agarose, 8 g of NaCl, 10 g of tryptone and 5 g of yeast extract in 900 ml of double distilled water, set the volume to 1 L by double distilled water, put the liquid in an autoclave, sterilize it at 121° C. for 20 minutes, cool it and store it at 4° C. for future use.

(6) TYE-AG solid medium:
Add ampicillin with final concentration of 100 μg/ml and glucose with a mass ratio of 1% to TYE solid medium.

(7) PBS solution:
Weigh 8.0 g of NaCl, 0.2 g of KCl, 2.9 g of $Na_2HPO_4.12H_2O$ and 0.2 g of $KH_2PO_4$, add them in distilled water respectively, dissolve them thoroughly and set the volume to 1 L.

(8) PBST solution:
0.05% PBST is prepared by adding Tween-20 with a volume ratio of 0.05% to PBS solution.
0.1% PBST is prepared by adding Tween-20 with a volume ratio of 0.1% to PBS solution.

(9) PEG/NaCl solution:
Weigh 20 g of PEG 8000 and 14.61 g of NaCl, add 80 ml of deionized water, set the volume to 100 ml, put the solution in an autoclave, sterilize it at 121° C. for 20 minutes, cool it and store it at 4° C. for future use.

(10) Citrate buffer solution (CPBS, substrate buffer solution, pH5.5):
Weigh 21 g of $C_6H_7O_8$ (citric acid) and 71.6 g of $Na_2HPO_4.12H_2O$, add them to distilled water respectively, dissolve them thoroughly and set the volume to 1 L.

(11) Tetramethyl benaidine (TMB) solution:
Weigh 10 mg of TMB, dissolve it in 1 ml of dimethyl sulfoxide, keep the solution in a dark place and store it at 4° C. for future use.

(12) Substrate chromogenic solution:
Composition of 10 ml formula: 9.875 ml of CPBS, 100 μl of TMB solution and 25 μl $H_2O_2$ with volume ratio of 20%.

(13) 3% MPBS solution:
Weigh 3 g of skim milk powder, dissolve it in 80 ml of PBS solution and add PBS solution to set the volume to 100 ml. HRP-goat anti-rabbit IgG described in the embodiment is diluted with 3% MPBS solution.

Sources of the materials involved in the embodiment:
BBMV, irrelevant Anti-Id single-chain antibody, non-"β"-type Anti-Id ScFv, cabbage leaves and Plutella xylostella third instar larvae were provided by the Key Laboratory for Agricultural Product Quality and Safety Control Technology and Standard of the Ministry of Agriculture, Jiangsu Academy of Agricultural Sciences;

Negative serum: The negative serum is collected from 1.5-2.0 kg purebred male New Zealand white rabbit. The collection time is one week prior to immunization;

Anti-Cry2Aa polyclonal antibody: Cry2A protein standard substance (Shanghai Youlong Biotech Co., Ltd.) is used as immunogen. Three 1.5-2.0 kg purebred male New Zealand white rabbits are selected as laboratory animals. The concrete immune procedure is as follows: in the first immunization, 200 micrograms of immunogen per rabbit is mixed with isovolumetric FCA (Freund's complete adjuvant). After the mixture is emulsified into an oil-in-water structure, it is subcutaneously injected at multiple points of the back (about 40 points). Two weeks later, it is enhanced by immunogen at the same dose and isovolumetric FIA (Freund's incomplete adjuvant). After that, it is enhanced once every two weeks. In the last time, immunogen is diluted with isovolumetric normal saline and then directly intravenously injected on ear margin. Eight days later, blood is collected from the heart, serum is prepared, thiomersalate with final concentration of 0.01% is added, and then the serum is purified by the method recorded in "Contemporary Immunological Technology and Application" (Ba Denian, United Press of Peking Medical University and Peking Union Medical College, 1998. 309-322) to obtain anti-Cry2Aa polyclonal antibody.

Humanized phage antibody library, TG1 bacteria and helper phage KM13 were purchased from British Source BioScience;
HRP-goat-anti-M13-IgG was purchased from Wuhan Boster Biological Technology Co., Ltd.;
Cry2Aa toxin and Cry1Ab toxin were purchased from Shanghai Youlong Biotech Co., Ltd.;
Paddy leaves and Cnaphalocrocis medinalis third instar larvae were provided by Yangzhou Luyuan Bio-Chemical Co., Ltd.

Embodiment 1: Screen Insecticidal Peptide (1) Add 20 µl of humanized phage antibody library bacterium liquid to 200 ml of 2×TY-AG fluid medium, cultivate it at constant temperature of 37° C. till $OD_{600}$ is 0.4, measure 50 ml of the bacterium liquid, add $1×10^{12}$ pfu of helper phage KM13 for superinfection, incubate the liquid at 37° C. for 30 minutes, then centrifuge it at 3300 g for 10 minutes, discard the supernate, use 100 ml of 2×TY-AKG fluid medium to resuspend the precipitate and cultivate it at 30° C. overnight; centrifuge it at 3300 g for 30 minutes next day, collect the supernate, add 20 ml of PEG/NaCl solution, keep it in ice bath for 1 h, then centrifuge it at 3300 g for 30 minutes and resuspend the precipitate by 4 ml of PBS; centrifuge the resuspension solution at 11600 g for 10 minutes. The supernate is amplified phage antibody library;

(2) Use the amplified phage antibody library obtained in step 1 for four rounds of Panning: The screening method is positive and negative screening. Negative serum is used for negative screening and anti-Cry2Aa polyclonal antibody is used for positive screening. A sequence of first negative screening then positive screening is adopted. Negative serum is coated in the negative cell culture flask. Anti-Cry2Aa polyclonal antibody is coated in the positive cell culture flask. The elution method adopts four rounds of competitive elution:

The first round of screening: Coat 4 mL of 100 µg/ml negative serum and 4 mL of 100 µg/ml anti-Cry2Aa polyclonal antibody to the bottom of the negative cell culture flask and that of the positive cell culture flask respectively, keep it at 4° C. overnight, wash the negative cell culture flask with PBS for 3 times next day, add 1 ml of amplified phage antibody library obtained in step 1, and 4 ml of 3% MPBS solution, put the flask on a shaking table, slowly shake it at room temperature for 1 h, let it rest for 1 h, wash the positive cell culture flask with PBS, suck the liquid in the negative cell culture flask, which has rested for 1 h, into the positive cell culture flask, put the flask on a shaking table, slowly shake it at room temperature for 1 h, let it rest for 1 h again, discard the liquid in the positive cell culture flask, wash the positive flask with 1 ml of 0.05% PBST for 10 times, add 1 ml of 10 mg/ml trypsin to elute the specifically bound phage antibody for 30 minutes. The eluent is phage antibody obtained in the first round of Panning.

The concentrations of the coated anti-Cry2Aa polyclonal antibody panned in the second, third and fourth rounds and negative serum are still 100 µg/ml. All the phage antibodies are the phage antibodies obtained from the previous round of panning. The panning method still adopts the strategy of positive and negative screening adopted in the first round. Different from the first round, in the second round, the positive flask is washed with 0.1% PBST solution for 10 times, 1 ml of 10 mg/ml trypsin is added to carry out competitive elution for 1 h; in the third and fourth rounds, the positive flask is washed with 0.1% PBST solution for 20 times and then 500 µl of 100 µg/ml Cry2Aa polyclonal antibody is added to substitute trypsin for competitive elution, the time of competitive elution in the third round is 1 h, and the time of competitive elution in the fourth round is 30 minutes.

10 µl of the phage antibody panned in the fourth round is used to infect 1 ml of TG1 bacteria in a logarithmic phase. After it is incubated at 37° C. for 1 h, it is coated on TYE-AG solid medium and cultivated at 37° C. overnight; next day, single colonies are picked randomly, incubated on a 96-well plate containing 100 µl/well of 2×TY-AG fluid medium and cultivated at 37° C. overnight; next day, 2 µl of bacterium liquid is sucked from the well plate, transferred to a new 96-well plate and incubated at 37° C. for 2 h. 25 µl of helper phage KM13 with titer of $10^{12}$ is added to every well, incubated at 30° C. for 2 h, centrifuged at 1800 g for 10 minutes, the precipitate is resuspended with 150 µl of 2×TY-AK fluid medium and then cultivated at 30° C. overnight. Next day, it is centrifuged at 1800 g for 30 minutes. The supernate is collected;

(3) 4 µg/ml anti-Cry2Aa polyclonal antibody is measured and added to a 96-well plate, 100 µl/well, and stored at 4° C. overnight. Next day, 100 µl of the supernate obtained in step 2 is added to every well. 100 µl of 2×TY-AK fluid medium is added to the negative control. They are kept in 37° C. water bath for 2 h. After the plate is washed with 250 µl/well of PBST, 100 µl of 1:5000 diluted HRP-goat-anti-M13-IgG is added to each well and incubated at 37° C. for 2 h. 100 µl of substrate chromogenic solution is added to each well and takes reaction at room temperature for 10 to 20 minutes till blue appears. Lastly 50 µl of 2 mol/L $H_2SO_4$ is added to each well to quickly terminate the reaction. $OD_{450}$ is determined by ELIASA. If $OD_{450}$ of the solution/$OD_{450}$ of negative control is greater than 2.1, it will be considered positive. The supernate in step 2 corresponding to this solution is the screened supernate containing anti-Cry2Aa toxin idiotype single-chain antibody, i.e.: the supernate of insecticidal peptide.

The nucleotide sequence of the screened insecticidal peptide determined by Sanger sequencing method is SEQ ID NO.1, as shown below:

```
ccggcccttt ggcatgcaat ttctatttca ggagacagtc ataatgaaat acctattgcc      60
tacggcagcc gctggattgt tattactcgc ggcccagccg gccatggccg aggtgcagct     120
gttggagtct gggggaggct tggtacagcc tgggggtgtcc ctgagactct cctgtgcagc    180
ctctggattc acctttagca gctatgccat gagctgggtc cgccaggctc cagggaaggg    240
gctggagtgg gtctcaagta ttgattctta tggtactaat acagattacg cagactccgt    300
gaagggccgg ttcaccatct ccagagacaa ttccaagaac acgctgtatc tgcaaatgaa    360
cagcctgaga gccgaggaca cggccgtata ttactgtgcg aaagctttta attcttttga    420
ctactggggc cagggaaccc tggtcaccgt ctcgagcggt ggaggcggtt caggcggagg    480
tggcagcggc ggtggcgggt cgacggacat ccagatgacc cagtctccat cctccctgtc    540
tgcatctgta ggagacagag tcaccatcac ttgccgggca agtcagagca ttagcagcta    600
tttaaattgg tatcagcaga aaccagggaa agcccctaag ctcctgatct atgctgcatc    660
cgctttgcaa agtggggtcc catcaaggtt cagtggcagt ggatctggga cagatttcac    720
```

```
tctcaccatc agcagtctgc aacctgaaga ttttgcaact tactactgtc aacagtatag    780
ttctagtcct tctacgttcg gccaagggac caaggtggaa atcaaacggg cggccgcaca    840
tcatcatcac catcacgggg ccgcagaaca aaaactcatc tcagaagagg atctgaatgg    900
ggccgcatag actgttgaaa gttgtttagc aaaacctcat acagaaaatt catttactaa    960
cgtctggaaa gacgacaaaa ctttaaatcg ttacgctaac                          1000
```

The amino acid sequence of the screened insecticidal peptide determined by Sanger sequencing method is SEQ ID NO.2, as shown below:

```
MKYLLPTAAAGLLLLAAQPAMAEVQLLESGGGLVQPGGSLRLSCAASGFTFSSYAMSWVR    60
           H-CDR2

QAPGKGLEWVSSIDSYGTNTDYADSVKGRFTISRDNSKNTLYLQMNSLRAEDTAVYYCAK   120
H-CDR3                      ----Link----

AFNSFDYWGQGTLVTVSSGGGGSGGGGSGGGGSTDIQMTQSPSSLSASVGDRVTITCRAS   180
L-CDR1                         L-CDR2

QSISSYLNWYQQKPGKAPKLLIYAASALQSGVPSRFSGSGSGTDFTLTISSLQPEDFATY   240
   L-CDR3                 His-tag

YCQQYSSSPSTFGQGTKVEIKRAAAHHHHHHGAAEQKLISEEDLNGAA                288
```

The applicant names this insecticidal peptide as F2.

Embodiment 2: Prepare Primary Culture of F2

The supernate obtained through screening in Embodiment 1 and containing insecticidal peptide is transferred to 10 ml of 2×TY-AG fluid medium at a volume ratio of 1:100 and incubated at 37° C. for 2 h. 100 μl of helper phage KM13 with titer of $10^{12}$ is added for rescue, incubated at 30° C. for 2 h and centrifuged at 1800 g for 10 minutes. The supernate is removed. 2×TY-AK fluid medium is used to resuspend the precipitated bacteria. It is cultivated while being shaken at 30° C. with 250 rpm overnight. Next day it is centrifuged at 1800 g for 30 minutes. Its supernate is supernate containing F2 primary culture.

Embodiment 3: Subtype Identification of F2

(1) ELISA Detection Experiment of Competitive Inhibition

The experiment adopts 6 experimental groups and corresponding control groups. Solutions are prepared based on Table 1.

TABLE 1

Preparation of solutions for ELISA detection experiment of competitive inhibition

| Group | F2 | Irrelevant Anti-Id single-chain antibody | 2 × TY fluid medium |
|---|---|---|---|
| Experimental group 1 | 5 μl |  | 45 μl |
| Control group 1 |  | 5 μl | 45 μl |
| Experimental group 2 | 10 μl |  | 40 μl |
| Control group 2 |  | 10 μl | 40 μl |
| Experimental group 3 | 20 μl |  | 30 μl |
| Control group 3 |  | 20 μl | 30 μl |
| Experimental group 4 | 30 μl |  | 20 μl |
| Control group 4 |  | 30 μl | 20 μl |
| Experimental group 5 | 40 μl |  | 10 μl |
| Control group 5 |  | 40 μl | 10 μl |
| Experimental group 6 | 50 μl |  |  |
| Control group 6 |  | 50 μl |  |

In Table 1, F2 is the supernate obtained in Embodiment 2 and containing F2 primary culture;

Add 50 μl of 10 μg/ml anti-Cry2Aa polyclonal antibody to the solutions prepared in Table 1 respectively, incubate them at 37° C. for 2 h, add them to a 96-well plate coated with 2 μg/ml Cry2Aa toxin respectively (the 96-well plate coated with 2 μg/ml Cry2Aa toxin is obtained by adding 2 μg/ml Cry2Aa toxin to a 96-well plate on the previous day, 100 μl/well and keeping it at 4° C. overnight), react for 2 h; wash the plate with 250 μl/well of PBST for 3 times, add 100 μl/well of 1:5000 diluted HRP-goat anti-rabbit IgG incubate it at room temperature for 1 h; wash the plate with 250 μl/well of PBST for 3 times, add 100 μl/well of substrate chromogenic solution, take reaction at room temperature for 10 to 20 minutes till blue appears and in the end add 50 μl/well of 2 mol/L $H_2SO_4$ to quickly terminate the reaction; determine $OD_{450}$ by ELIASA.

The experimental results are as shown in FIG. 1. The inhibition ratio increases with the increase of F2 content. The control groups do not have the phenomenon of competitive inhibition, suggesting F2 is β-type Anti-Id single-chain antibody and can simulate Cry2Aa toxin to competitively bind with anti-Cry2Aa toxin polyclonal antibody.

(2) Biological Determination Experiment

The experiment has experimental group 1, experimental group 2, experimental group 3, positive control group, negative control group 1, negative control group 2 and negative control group 3; the experimental procedure is as follows:

(a) Blocking: Coat 100 μl/well of 5 μg/ml BBMV in a 96-well plate, keep it at 4° C. overnight, wash the plate with 250 μl/well of PBST for 3 times next day, add 200 μl of BAS with a mass ratio of 3% respectively, incubate it at room temperature for 2 h, and carry out blocking;

(b) Sample addition: Wash the 96-well plate blocked in step 1 with 250 μl/well of PBST for 3 times, and add samples to the 96-well plate according to Table 2:

TABLE 2

Preparation of solutions for biological determination experiment of F2

| Group | 2 µg/ml Cry2Aa toxin | F2 | Non-"β"-type Anti-Id ScFv | 2 × TY-AG fluid medium | CPBS |
|---|---|---|---|---|---|
| Experimental group 1 | 50 µl | 10 µl | | 40 µl | |
| Experimental group 2 | 50 µl | 30 µl | | 20 µl | |
| Experimental group 3 | 50 µl | 50 µl | | | |
| Positive control group | 50 µl | | | | 50 µl |
| Negative control group 1 | 50 µl | | 10 µl | 40 µl | |
| Negative control group 2 | 50 µl | | 30 µl | 20 µl | |
| Negative control group 3 | 50 µl | | 50 µl | | |

In Table 2, F2 is the supernate obtained in Embodiment 2 and containing F2 primary culture;

(c) Incubate the 96-well plate added with sample in step b at room temperature for 2 h, wash the plate with 250 µl/well of PBST for 3 times, add 100 µl/well of 10 µg/ml anti-Cry2Aa polyclonal antibody, then wash the plate with 250 µl/well of PBST for 3 times, add 100 µl/well of 1:5000 diluted HRP-goat anti-rabbit IgG and incubate it at room temperature for 1 h; wash the plate with 250 µl/well of PBST for 3 times, add 100 µl/well of substrate chromogenic solution per well, take reaction at room temperature for 10 to 20 minutes till blue appears and in the end add 50 µl/well of 2 mol/L $H_2SO_4$ to quickly terminate the reaction, and determine $OD_{450}$ by ELIASA.

Figure 2:
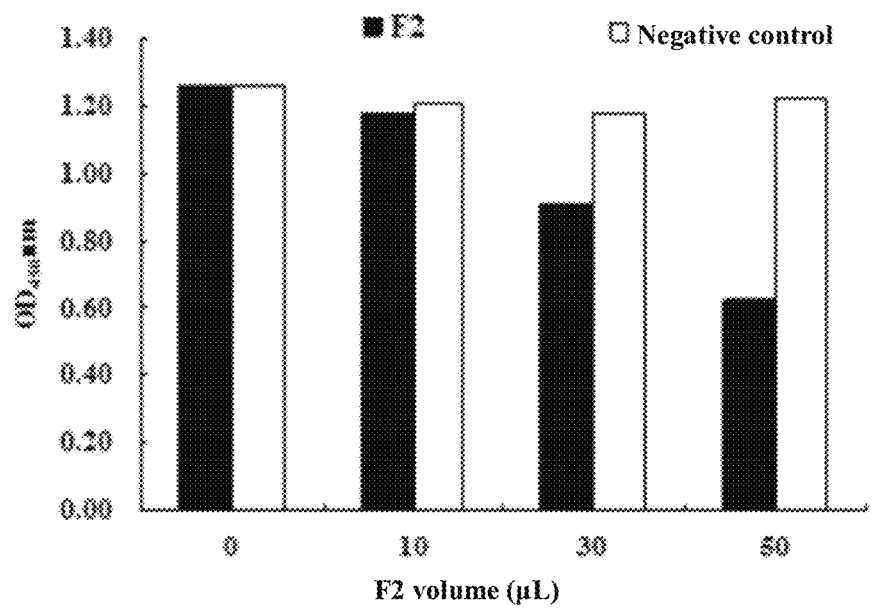
FIG. 2 is a schematic of F2 biological determination result.

The experimental result is as shown in FIG. 2. Compared with positive control, insecticidal peptide F2 (Experimental groups 1, 2 and 3) can inhibit the binding between Cry2Aa toxin and its receptor BBMV; non-"β"-type negative control does not have the phenomenon of inhibition, which further proves that F2 is "β" type.

Embodiment 4: Verify Insecticidal Activity of Insecticidal Peptide F2

The experiment has experimental groups and control groups:
The experimental groups use the supernate (F2) obtained in Embodiment 2 and containing F2 primary culture;
The positive control groups adopt 0.2 g/L Cry1Ab toxin (CK+);
The negative control groups adopt non-"β" type Anti-Id ScFvs (CK−);

Experimental Procedure:
Measure experimental groups, positive control groups and negative control groups each 10 ml, put them in sterilized culture dishes, add 6 paddy leaves and 6 cabbage leaves respectively, soak them for 30 minutes, take them out and dry them in the air; feed *Cnaphalocrocis medinalis* third instar larvae and *Plutella xylostella* third instar larvae with dried leaves.

Figure 3:
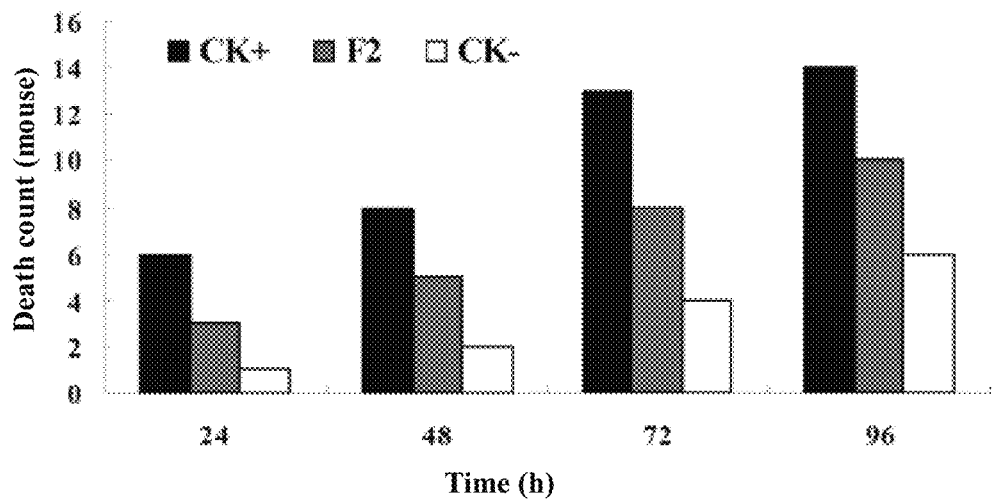
FIG. 3 is a schematic showing the death condition of Cnaphalocrocis medinalis third instar larvae after they were fed with paddy leaves soaked with F2, CK+ and CK− respectively.
Figure 4:
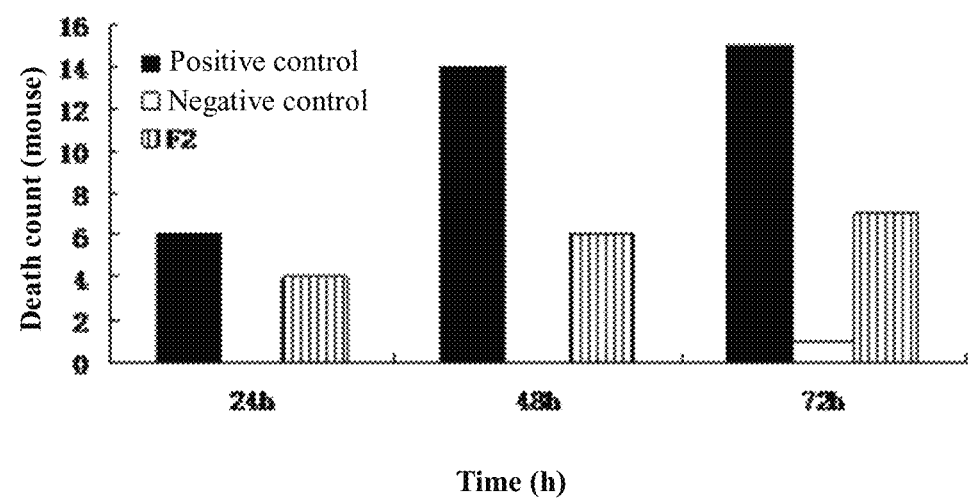
FIG. 4 is a schematic showing the death condition of Plutella xylostella third instar larvae after they were fed with cabbage leaves soaked with F2, CK+ and CK− respectively.

The experimental result is as shown in FIG. 3 and FIG. 4. FIG. 3 shows the death condition of *Cnaphalocrocis medinalis* third instar larvae respectively fed with paddy leaves, which have been soaked with experimental groups (F2), positive control groups (CK+) and negative control groups (CK−). FIG. 4 shows the death condition of *Plutella xylostella* third instar larvae respectively fed with cabbage leaves, which have been soaked with experimental group (F2), positive control group (CK+) and negative control group (CK−). It can be seen that insecticidal peptide F2 in the experimental groups has a good insecticidal effect.

The invention claimed is:
1. A polynucleotide comprising SEQ ID NO.1.
2. A prokaryotic vector comprising the polynucleotide of claim 1.

* * * * *